(12) United States Patent
Hlavaty (10) Patent No.: US 7,835,873 B2
(45) Date of Patent: Nov. 16, 2010

(54) METHOD AND SYSTEM FOR MONITORING CHANGES IN A SAMPLE FOR A PROCESS OR AN ENVIRONMENT

(75) Inventor: Charles W. Hlavaty, O Fallon, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/058,171

(22) Filed: Mar. 28, 2008

(65) Prior Publication Data

US 2009/0248342 A1 Oct. 1, 2009

(51) Int. Cl.
*G01N 31/00* (2006.01)
(52) U.S. Cl. .................................................. 702/31
(58) Field of Classification Search ................ 702/31
See application file for complete search history.

(56) References Cited

U.S. PATENT DOCUMENTS

| | | | |
|---|---|---|---|
| 5,939,721 A | 8/1999 | Jacobsen et al. | |
| 6,747,736 B2 | 6/2004 | Takahashi | |
| 6,815,683 B2 | 11/2004 | Federici et al. | |
| 7,663,107 B2 | 2/2010 | Taday | |
| 2003/0100824 A1* | 5/2003 | Warren et al. | 600/407 |
| 2004/0095147 A1 | 5/2004 | Cole | |
| 2004/0227088 A1 | 11/2004 | Trotz et al. | |
| 2005/0056785 A1 | 3/2005 | Chou et al. | |
| 2006/0231762 A1 | 10/2006 | Ohtake et al. | |
| 2007/0010702 A1* | 1/2007 | Wang et al. | 600/8 |
| 2007/0114419 A1 | 5/2007 | Bastiaans et al. | |

(Continued)

OTHER PUBLICATIONS

Katharyn S. Kalasinsky, Ted Hadfield, April A. Shea, Victor F. Kalasinsky, Matthew P. Nelson, Jason Neiss, Amy J. Drauch, G. Steven Vanni, and Patrick J. Treado, Raman Chemical Imaging Spectroscopy Reagentless Detection and Identification of Pathogens: Signature Development and Evaluation, Analytical Chemistry, Apr. 1, 2007, 2658-2673, vol. 79, No. 7, US.

(Continued)

*Primary Examiner*—Aditya Bhat
(74) *Attorney, Agent, or Firm*—Moore & Van Allen PLLC; Charles L. Moore (57) ABSTRACT

Systems and methods for monitoring a sample or a sample flow associated with a process or an environment are disclosed. The systems and methods are used detect one or more chemical or biological agents present in a sample or detect changes in the chemical/biological composition of a sample flow. The systems and methods transmit light at the sample, perform spectral analysis of the resulting spectral response, and display a result or choose a course of action. The analysis compares the sample's response to known spectrums to determine composition or to determine if the composition of the sample has deviated from "normal". In one embodiment, the systems and methods uses deep ultraviolet light to produce both a Raman and a fluorescence response, separated in frequency, which are simultaneously discerned and analyzed. In this embodiment the analysis is used to determine sample composition or to discern or warn of changes, or to choose a course of action.

37 Claims, 4 Drawing Sheets

U.S. PATENT DOCUMENTS

| | | | |
|---|---|---|---|
| 2008/0106733 A1* | 5/2008 | Swift et al. | 356/317 |
| 2008/0203306 A1 | 8/2008 | Zhang et al. | |
| 2008/0258071 A1 | 10/2008 | Arnold et al. | |
| 2009/0065697 A1 | 3/2009 | Siegel et al. | |
| 2009/0206263 A1 | 8/2009 | Rahman | |

OTHER PUBLICATIONS

Campbell et al., "Non-Invasive Detection of Weapons of Mass Destruction Using THz Radiation"; 2003, SPIE, vol. 5070, pp. 38-43.

Woolard et al., "Terahertz-Frequency Remote Sensing of Biological Warfare Agents"; 2003 IEEE, pp. 763-766.

* cited by examiner

*Excitation-Emission-Matrix diagram of benzene*

| Plot No. | Organism | Mole% G+C | Gram | Spores | Virulence class[g] |
|---|---|---|---|---|---|
| | Clostridium botulinium | 28.2[i] | + | X | 2 |
| | Rickettsia prowasecki | 28.9[i] | - | | 3 |
| | Staphylococcus aureus | 32.8[b] | + | | 2 |
| 1 | Bacillus cereus | 32[a] | + | X | 1 |
| 2 | Enterococcus faecalis | 34-36[a] 37.5[b] | - | | 1 |
| | Staphylococcus simulans | 34-38[a] | + | | 1 |
| | Bacillus antracis Ames | 35.2[b] | + | *X* | 2 |
| | Streptococcus agalactiae | 35.5[b] | + | | 1 |
| 4 | Proteus vulgaris | 36-40[a] | - | | 1 |
| 3 | Bacillus magaterium | 37[a] | + | X | 1 |
| 5 | Proteus mirabilis | 39.5[a] | - | | 1 |
| 6 | Bacillus subtilis | 41[a] | + | X | 1 |
| 7 | Acinetobacter calcoaceticus | 42[a] | - | | 2 |
| | Bacillus subtilis | 43.5[b] | + | X | 1 |
| | Shewanella oneidensis MR1 | 45.9[b] | - | | 1 |
| | Yersinia pestis. | 47.6[i] | - | | 3 |
| | Vibrio cholerae | 47.6[i] | - | | 3 |
| 8 | Escherichia coli, K12-MG1655 | 50.7[b] | - | | 2 |
| | Shigella dysenteriae | 50[i] | - | | 2 |
| | Samonella tphi | 52.1[i] | - | | 2 |
| 9 | Enterobacter aeroqenes | 54.3[a] | - | | 1 |
| 10 | Alcaliqenes faecalis | 54.8[a] | - | | 1 |
| 11 | Enterobacter cloacae | 55.4[a] 57.2[b] | - | | 1 |
| 12 | Aeromonas hydraphila | 55.7[a] | - | | 1 |
| | Brucella suis 1330 | 57.2[b] | - | | 3 |
| | Brucella melitensis | 57.2[c] | - | | 3 |
| | Aeromonas hydrophila | 59-62[c] | - | | 1 |
| | Pseudomonas putida | 61.4 | - | | 1 |
| 13 | Pseudomonas aeruqinosa | 64[a],66.4[b] | - | | 1 |
| 14 | Micrococcus luteus | 66.3[a] | + | | 1 |
| | Alcaligenes faecalis | 66.7-69.9 | - | | 1 |
| | Burkholderia pseudomallei | 68.06[i] | - | | 3 |
| | | | | | |

Figure 5

METHOD AND SYSTEM FOR MONITORING CHANGES IN A SAMPLE FOR A PROCESS OR AN ENVIRONMENT

BACKGROUND OF THE INVENTION

The present invention relates generally to detection of the composition of a sample, and more particularly to methods and systems for detecting chemical and/or biological agents in a sample or samples or detecting a chemical/biological change in composition of a sample flow.

Various testing systems have been developed to detect harmful biological agents in samples. Many of these conventional systems use chemical reactions applied to a contained sample over a given time period. By monitoring these chemical reactions, an analysis of the sample is made and identifications of biological agents, if present, are determined. While these conventional systems provide accurate results, there are many drawbacks associated with their use.

In particular, there may be significant delay between the time the sample is received and the results are determined. Chemical reactions take time to occur and process, which introduces delay. Further, systems that use chemical reactions as part of sample testing may require special environmental considerations (e.g., space, temperature control, specialized equipment, etc.) that may make use of such systems impractical for some applications. Chemical reaction analysis solutions are generally complex, too large, and too heavy. They often require sample preparation and minutes to hours to obtain results. Further, they may be limited to a discrete number of analyses before the equipment must be reset or the chemicals used in the reactions replaced.

BRIEF SUMMARY OF THE INVENTION

The present invention provides systems and methods for detecting changes in a sample and/or the presence of one or more of a chemical and/or a biological agent present in a sample. The systems and methods use spectral analysis, rather than chemical reactions, to assess the content of the sample. The systems and methods thus eliminate the complex mechanisms needed for sample collection, concentration, isolation, and preparation to obtain a chemical reaction. Where a chemical-based solution is limited to a discrete number of analyses between replenishment of supplies, the systems and methods of the present invention may provide real time, continuous, near real time, or substantially continuous analysis of a sample or sample flow.

These advantages mean that the systems and methods of the present invention may be used for real-time evaluation. For example, when used in a vehicle, the systems and methods may be used to map a hazardous plume, or help guide a vehicle to either seek the area of highest concentration, or turn to avoid the hazardous plume. It can also be used as an alarm to declare that vehicle decontamination must be accomplished due to exposure to hazardous material and identify the contents of exposure. Its real-time or near real-time capability immediately informs vehicle occupants that they should take appropriate actions due to exposure, enables immediate broadcast of warnings to others nearby, and its material identification can help guide choices in immediate medical treatment. By digitally recording measurements of spectral signatures, the systems and methods may provide a permanent record that can be used to substantiate exposures or enable further analysis post mission.

The systems and methods of the present invention may also be used to control various processes. For example, the system and methods may be used to monitor a sample associated with a process. The systems and methods of one embodiment may be used to provide alerts when a content of the sample reaches a threshold level. The systems and methods of some embodiments may provide feedback to the process for altering the process based on the analysis of a sample. In some embodiments, the systems and methods may further determine a cause for changes in the process that caused the level of content of a sample and may provide feedback to the process to regulate its control mechanisms.

In one embodiment, an apparatus is provided for monitoring a sample or a sample flow. The apparatus comprises an emitter for positioning relative to a sample. The emitter is capable of emitting a light signal directed at the sample. A detector is positioned relative to the sample to receive a resulting spectral response signal following interaction of the emitted signal with the sample. Further, a processing element in communication with the detector is capable of:

performing analysis of the resulting spectral response signal;

determining deviation of the spectral response from an expected response;

determining the cause of the deviation based on spectral response analysis;

determining a value indicating the extent or severity of deviation from the expected response;

comparing the value to a threshold; and issuing an alert if the value is at least as great as the threshold.

In one embodiment, the processing element is capable of:

performing analysis of the resulting spectral response signal;

determining one or more chemical and/or biological agents present in the sample;

determining a value indicating one of an amount or a percentage of the chemical and/or biological agent in the sample;

comparing the value to a threshold; and issuing an alert if the value is at least as great as the threshold.

The systems and methods of the present invention may be implemented in a wide range of configurations and embodiments. As an example, the systems and methods may be employed on a vehicle to assess chemical and/or biological agents in the air. In this embodiment, the sample may be "captured in" or "flowed through" a chamber, such as a tube, for analysis. A series of one or more filters may be employed to process the sample prior to testing. For example, an inlet design and tube design may utilize flow dynamics to filter out wrong-sized particulates in the air, to slow down the sample, and to compress or concentrate the sample prior to analysis.

In one embodiment, the emitter is capable of emitting a laser signal in the deep ultraviolet spectrum. The processing element is capable of performing spectral analysis of the resulting spectral response signal using both Raman scattering spectrum analysis and by analyzing the fluorescence response. The analysis determines whether the sample includes chemical and/or biological agents, or whether the sample has deviated from a "normal" spectral response. In the latter case, the analysis can then either produce a warning, or choose an appropriate course of action to effect a desired change to the sample flow.

In one embodiment, processing element collects measurements from the sample over time and determines from the collected measurements the presence of one or more chemical and/or biological agents in the sample. In added or alternative embodiments, the processing element collects measurements from the sample from different locations within the sample and determines from the collected measurements the presence of one or more chemical and/or biological agents in the sample. In further added or alternative embodiments, the processing element collects measurements from the sample over different frequencies and determines from the collected measurements the presence of one or more chemical and/or biological agents in the sample.

Other aspects and features of the present invention, as defined solely by the claims, will become apparent to those ordinarily skilled in the art upon review of the following non-limited detailed description of the invention in conjunction with the accompanying figures.

DETAILED DESCRIPTION OF THE INVENTION

The following detailed description of embodiments refers to the accompanying drawings, which illustrate specific embodiments of the invention. Other embodiments having different structures and operations do not depart from the scope of the present invention.

As will be appreciated by one of skill in the art, the present invention may be embodied as a method, system, or computer program product. Accordingly, portions of the present invention may take the form of an entirely hardware embodiment, an entirely software embodiment (including firmware, resident software, micro-code, etc.) or an embodiment combining software and hardware aspects that may all generally be referred to herein as a "circuit," "module," "unit," or "system." Furthermore, the present invention may take the form of a computer program product on a computer-usable storage medium having computer-usable program code embodied in the medium.

Any suitable computer-usable or computer-readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a tangible medium such as a portable computer diskette, a hard disk, a random access memory (RAM), a read-only memory (ROM), an erasable programmable read-only memory (EPROM or Flash memory), an optical fiber, a portable compact disc read-only memory (CD-ROM), or other tangible optical or magnetic storage devices; or transmission media such as those supporting the Internet or an intranet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or other programming languages such as object code or assembly language. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The present invention provides systems and methods for detecting one or more of a chemical and/or a biological agent present in a sample, or to determine if the sample has deviated from "normal". The systems and methods use spectral analysis, rather than chemical reactions, to detect and assess the presence of chemical and/or biological agents. The systems and methods thus allow for elimination of complex mechanisms needed for sample collection, concentration, isolation, and preparation to obtain a chemical reaction. Where a chemical-based solution is limited to a discrete number of analyses between replenishment of supplies; the systems and methods of the present invention may provide real time, continuous, near real time, or substantially continuous analysis of a sample.

The systems and methods of the present invention thus may be used for real-time evaluation. For example, when used in a vehicle, the systems and methods may be used to map a hazardous plume, or help guide a vehicle to either seek the plume or turn to avoid it. It can also be used as an alarm to declare that vehicle decontamination should be accomplished due to exposure to hazardous material; and it can help identify the contents of exposure. The real-time capability of the systems and methods of the present invention immediately informs vehicle occupants that they should take appropriate actions due to exposure, enables immediate broadcast of warnings to others nearby, and its material ID can help guide choices in immediate medical treatment. By digitally recording its measurements of spectral signatures, it may provide a permanent record that can be used to substantiate exposures or enable further analysis post mission. Various sensors could be distributed in a network to provide area wide warnings and mapping capabilities.

The embodiments below discuss the systems and methods of the present invention in the context of a chemical/biological agent detector mounted in a vehicle such as an aircraft, car, etc. It is understood, however, that the systems and methods are not limited to this application, but instead may be used in any environment or system where chemical and/or biological testing is needed, or may be used to monitor sample flows to determine if the sample has deviated from "normal" and determine how to effect a change that will return the sample flow to "normal".

Figure 1:
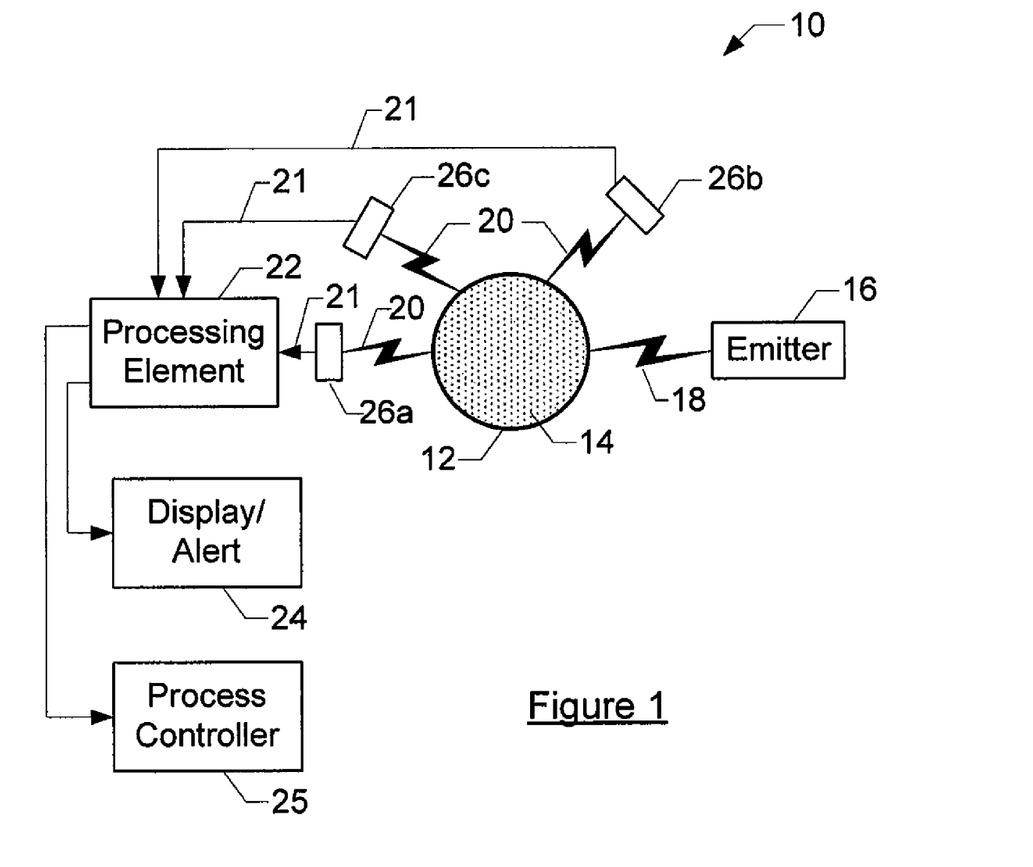
FIG. 1 is a block schematic diagram of a system for detecting one or more of a chemical and/or a biological agent present in a sample or sample flow, or for determining that a change has occurred to the sample or sample flow according to one embodiment of the present invention.

FIG. 1 illustrates a general embodiment of the invention. As illustrated, in this embodiment, the system 10 includes a sample chamber or tube 12 for "capturing" and/or otherwise housing a sample or sample flow 14 of a gas, liquid, or solid. For example, in one embodiment, the system could be used with a vehicle, where the tube 12 is placed in a location so as to process air samples or water samples in the environment surrounding the vehicle.

Associated with the sample tube 12 is an emitter 16 for transmitting a light signal 18 directed at the sample. One or more detectors 26 are provided to receive the resulting spectral response signal 20 after the light signal has interacted with the sample 14. Further, a processing element 22 is connected to or in communication with the detectors 26 for analyzing the resulting spectral response 21 obtained from the detectors 26. The processor is connected to a display and/or an alert 24 to provide an indication if the sample includes one or more chemical and/or biological agents, and/or to a process controller 25 to cause a change that will affect the composition of the sample flow.

In one embodiment, the processing element may be a computer or computing element comprising a general processor. The processing element of this embodiment may further include or have associated therewith a storage device comprising computer instructions for receiving and processing the resulting signal. For example, the storage may include various algorithms in the form of computer programming to implement known analysis procedures for identifying chemical and/or biological agents. It may also contain spectral response patterns for use in the analysis.

As illustrated in FIG. 1, depending on the type of set up, different detectors at different locations may be used. For example, detector 26a is positioned to receive a resulting signal propagated through the sample for analysis. Detector 26b, on the other hand, is positioned to receive a reflected signal from the sample. Detector 26c may represent an instance where multiple sensors are used at various locations to collect resulting signals from the sample. Depending upon the dynamic range of the detector, the direct path may need a light trap mechanism in lieu of 26a to reduce unwanted reflections of the light signal 18 into the detector 26b, 26c.

In a general manner, a light signal is directed at the sample 14. This light signal induces a spectral response from the sample. The resulting spectral response signal 20 is received and measured by the detector 26 which embodies an optical spectrometer. The spectrometer measures the received light intensity as a function of the light's frequency. Measurements from the detector, i.e., the spectral response, are output 21 to the processing element for analysis using various techniques. These techniques compare the measured spectral response to previously measured spectral responses of known chemical and/or biological agents to determine the composition of the sample. When used with the process controller 25, the techniques could compare the measured response to previously measured responses of "normal" and "non-normal" sample flows to determine if a deviation has occurred, and how best to react to the deviation based upon its measured spectral response. This information is used by the process controller 25 to alter the process.

In general, spectral analysis is employed to analyze the sample. In spectral analysis, the spectral response signal 20 is spread spatially in frequency and the intensity vs. frequency is measured using a detector or focal plane array. Various chemicals and biological agents produce a different spectral intensity vs. frequency output that is characteristic of that chemical or biological agent. This spectral output is a "signature" or fingerprint for the chemical, biological agent, or sample flow. By comparing the spectral response 21 of the measured signal to the known spectral responses for known chemicals and biological agents, the composition of the sample 14 can be determined. In addition, by comparing the spectral response 21 to known spectral responses of the sample flow, deviations can be discerned, identified, and a course of action chosen; either to correct the sample flow back to its normal state via the process controller 25 or to affect some other desired outcome.

Spectral analysis provides several advantages over conventional chemical reaction testing. It allows continuous, real-time, non-destructive testing of the sample flow. Continuous testing always observes the sample. Real-time testing produces results without appreciable delay. Non-destructive testing does not consume, change, or destroy the sample. These characteristics make this system applicable for use in applications where real-time control based upon the sensed sample flow is needed to control a process or determine courses-of-action. In addition, spectral analysis does not require chemical or other resources (other than electricity) to perform the test. Thus, the system typically does not require the daily or periodic cleaning and maintenance that other systems require.

It is understood that various types of spectral analysis may be used with the present invention. In one particular embodiment of the present invention, simultaneous Raman and fluorescence spectrum analysis is used to determine the chemicals and/or biological agents in a sample. Each phenomena can be used separately to discern and identify chemicals and biological agents. Further, the phenomena could be measured in a stepwise fashion, first measuring one response, then measuring the other. However, by simultaneously measuring and processing both responses, better discernment can be obtained in real-time.

Figure 3A:
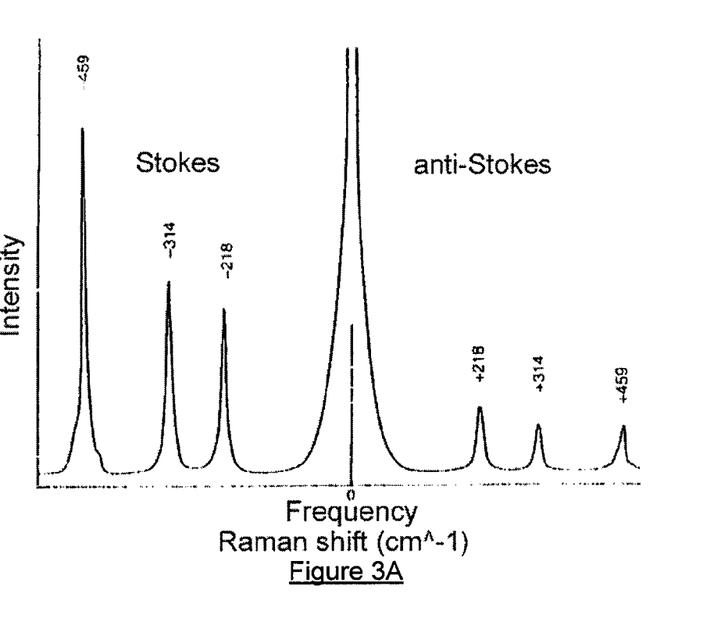
FIG. 3A is graphic illustration of Raman shift in the frequency domain.

The Raman response is associated with the scattering of light; however, the Raman response scatters the incident light with a plus and minus delta frequency change from the incident light's frequency, see FIG. 3a. Fluorescence, when produced, is a light emission that various chemicals and biological agents emit after they absorb the incident light. The fluorescence frequency is independent of the incident light's frequency.

Raman response can occur for incident light whose frequency is too low to cause a fluorescence effect. But this response is generally a weak response. When the incident light frequency is nearly sufficient for fluorescence, a stronger response, called resonance Raman, occurs; however, the response can be masked by fluorescence emissions from that particular chemical or others in the sample. The overlap of responses can increase the difficulty in discerning a sample's composition.

Figure 3B:
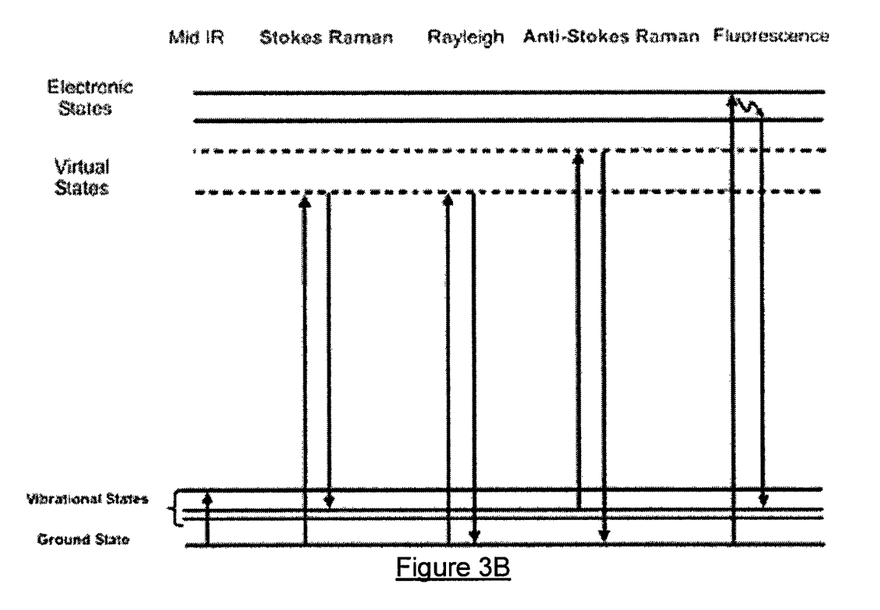
FIG. 3B is a graphic illustration of the states of a molecule depicting the difference between Raman and fluorescence responses of the molecule.

FIG. 3b contrasts the different phenomena involved with Raman and fluorescence. Raman relates to vibrational states of the sample; fluorescence relates to the electronic states of the sample. Taken together, these signatures provide a more complete picture of the sample composition. For a given sample, one can choose the illumination frequency so that the two phenomena do not overlap. But for general conditions, this cannot be achieved since a wide range of materials fluoresce between 260 nm and 750 nm. However, By using deep UV (200-240 nm) as an illuminator, the two phenomena will not overlap.

Figure 4:
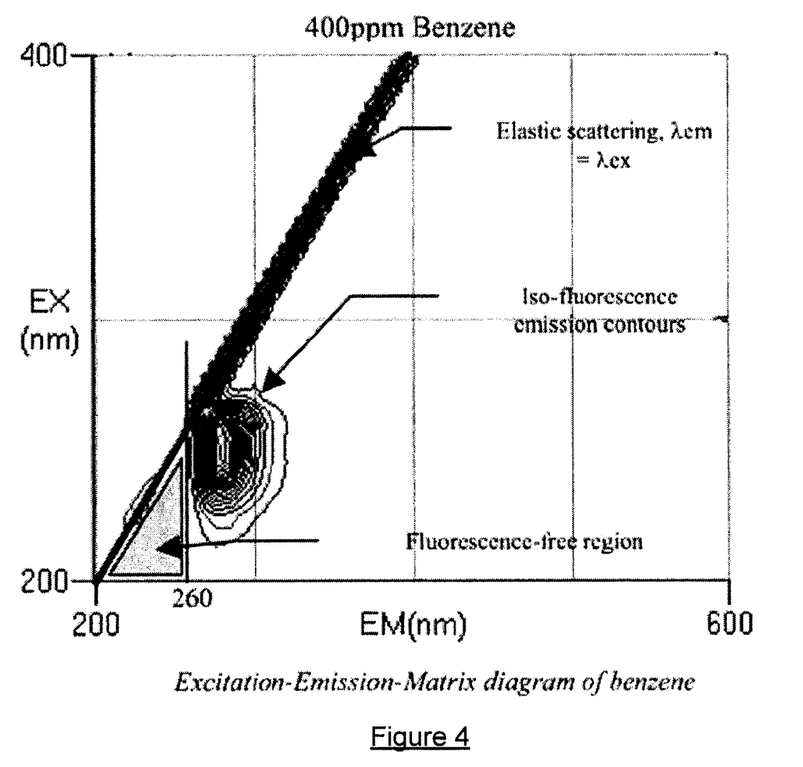
FIG. 4 is a graphic illustration of the fluorescence and Raman emittance of a molecule excited by a light signal.

As an example, FIG. 4 illustrates the excitation-emission matrix for benzene. Note that its fluorescence occurs at 260 nm and longer wavelengths. But the band of Raman scattering is depicted as an EM delta from the EX wavelength (the widened elastic scattering line). When the excitation (EX) is deep UV, Raman scatter wavelengths occur in the fluorescence-free region and will not overlap fluorescence emission wavelengths for benzene or other material (260 nm to 750 nm).

In light of the above, to generate a resulting spectral response signal that includes both Raman and fluorescence separated in frequency for simultaneous discernment and analysis, one embodiment of the present invention uses deep ultraviolet light signals 18. Deep ultraviolet includes wavelengths in the range of 200 nm to 240 nm. Deep ultraviolet generates a spectral response signal that includes both Raman and fluorescence separated in frequency so that both can be simultaneously measured and analyzed.

The goal for the detector 26 in this embodiment is to physically spread the spectral response signal 20 so that its intensity vs. frequency can be measured by a detector or a series of detectors (such as a focal plane array). One embodiment uses a diffraction grating system (FIG. 2) with an entrance slit for the spectral response signal (light), a series of mirrors to fold/control the optical path, a diffraction grating to cause the light to spatially spread out in frequency, and a detector (focal plane array) to sense the light's intensity vs. position on the array. The pixel location across one axis of the array measures the spectral response signal's intensity for a particular frequency; the pixel location across the other axis measures the spectral response signal's intensity for different optical locations across the length of the slit entrance (different optical paths across the sample tube). The focal plane array provides an array of pixel measurements according to its performance, typically multiple array measurements per second. These measurements are the output (spectral response 21) from the detector 26.

Figure 2:
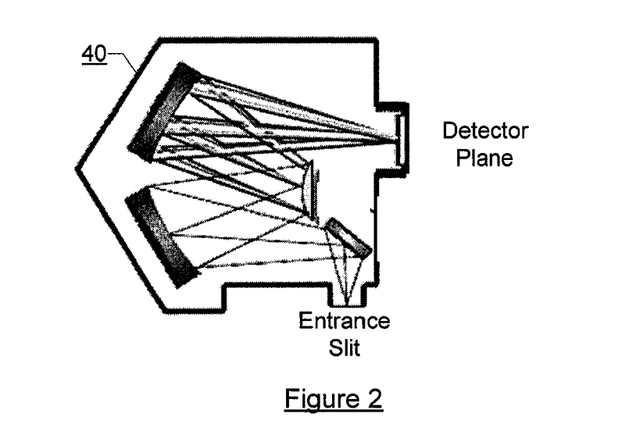
FIG. 2 is a block schematic diagram of one embodiment of a detector according to one embodiment of the present invention in which mirrors, diffraction grating, and a focal plane array are used to determine the spectral response of a sample to an emitted light.

The spectral response is then processed by the processing element 22. Analysis algorithms are used to discern the material makeup from the observations. In one embodiment, the spectral response (pixel locations for intensity vs. frequency) for one time frame are analyzed. Another embodiment combines the spectral response across multiple time frames. Still another embodiment combines the spectral response for one or more time frames for multiple optical locations across the slit. These data are analyzed and compared to thresholds, sample patterns (spatial, time or both), or other methods to either discern the content of the sample or to discern a deviation from normal.

Figure 5:
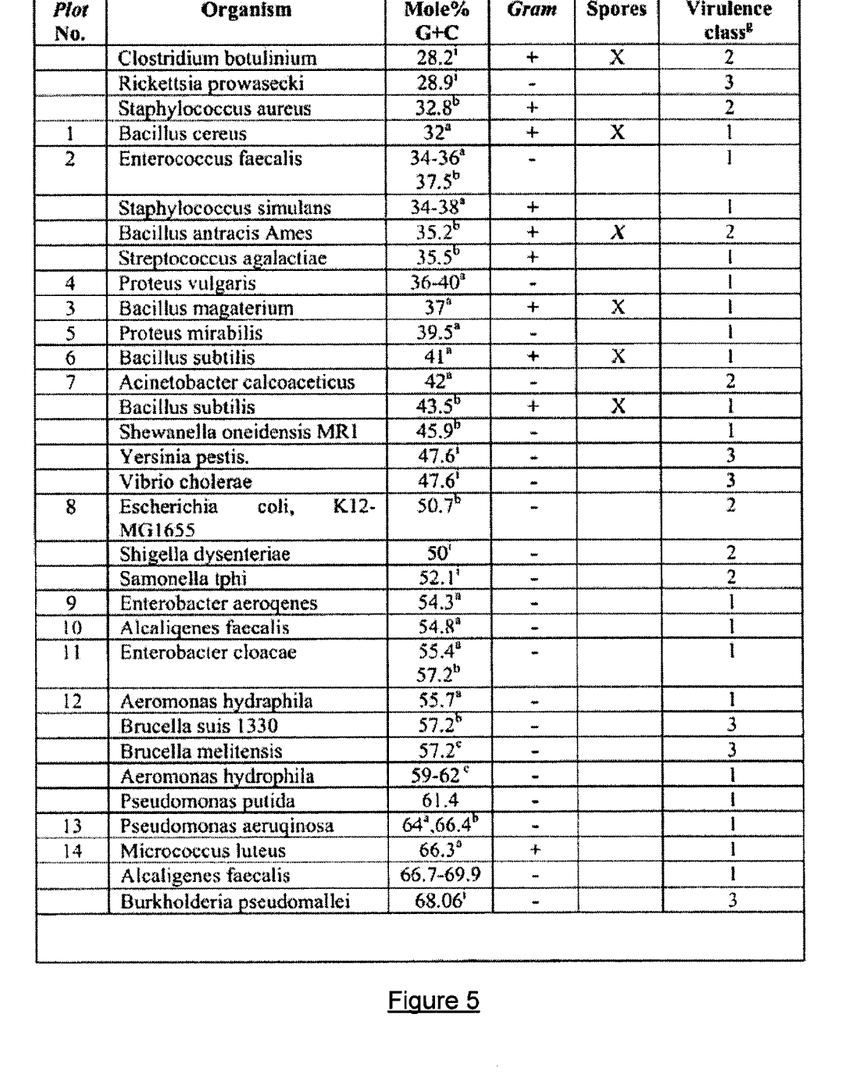
FIG. 5 is a graphic table illustrating an analysis of a sample using Raman scatter and fluorescence.

With reference to FIG. 5, one published detection and identification strategy for biological agents using laser induced fluorescence and Raman spectroscopy is as follows:

Determine if a particle is biological or non-biological based on measuring laser induced fluorescence in the 300 nm region;

If the particle is biological, measure the relative UV Raman intensity at five (5) Raman bands centered at 1017 cm−1, 1485 cm−1, 1530 cm−1, 1555 cm−1, and 1615 cm−1;

Determine if the particle is Gram positive or negative based on 1555 cm−1/1615 cm−1 ratio;

Determine if the particle is a spore based on the 1017 cm−1/1615 cm−1 ratio; and Determine the GC % based on the 1530 cm−1/1485 cm−1 ratio.

FIG. 5 is referenced from the following source "Deep UV Laser Diode for UV Resonance Enhanced Raman Identification of Biological Agents", Photon Systems, DARPA SBIR Final Report, Contract W31 P4Q-04-C-R039, pp 137, May 31, 2007, the contents of which are incorporated herein by reference.

Based upon the results of the analysis, the systems and methods of the present invention have a wide variety of application. The systems and methods may be used in conjunction with a vehicle to analyze the environment surrounding the vehicle and provide alerts where chemical and/or biological agents are detected. This could be used to alert the occupants of danger, such that the occupants can take action to alter either their current route or location, seek decontamination of the vehicle, seek medical help, etc.

More specifically, in this embodiment, samples of the environment associated with the vehicle are captured and subjected to a test signal. The resulting spectral response signal is detected and analyzed for chemical and/or biological agents. Depending either on the type of agent and/or the level of the agent in the environment, the system generates alarms to the occupants and/or transmits alarms to remote locations to indicate potential danger, decontamination procedures should be employed, and/or medical help needed.

By continuing to take readings and provide alerts, the systems and methods could be used to "steer" the user of the vehicle to avoid the area where the chemical and/or biological agent is located. The system would provide information regarding changes in level of the detected chemical and/or biological agent over time.

Alternatively, the systems and methods could be used to "steer" the user of the vehicle toward the source or increased concentration of the chemical and/or biological agent, where the function of the vehicle to scout and pin point the source of the chemical and/or biological agent.

The systems and methods could also be used for early warning to other vehicles. For example, if two or more vehicles are traveling in an area and if the first vehicle detects a chemical and/or biological agent, it may alert the other vehicle to take evasive action. In this embodiment, the vehicle may include a transmitter capable of transmitting the alert to a remote location.

In some embodiments, the systems and methods could be used to map a geographic area. One or more vehicles may be deployed to take various sample readings over a given area and provide feedback regarding the presence of chemical or biological agents in a given area. In this embodiment, the vehicles navigation system is used to map the locations of various levels of the chemical and/or biological agent. When coupled with GPS readings, this information can provide an effective map of the expanse of the chemical and/or biological agent dispersion.

Additionally, the systems and methods could be used to monitor a manufacturing process to detect if and when the process deviated from normal. With appropriate design and calibration, the systems and methods could also identify what response should be executed to bring the process back to normal. In these embodiments, the response could be based on determining the chemical/biological content of the sample, or it could be based on a comparison of the sample's measured spectrum to previously measured spectrums that were associated with particular responses.

Specifically, in addition to including algorithms and/or computer code to detect chemical and/or biological agents, the systems and methods may include algorithms and methods that provide feedback information to a process to alter the process to thereby alter the level of the detected chemical and/or biological agent.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a" "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. An apparatus for monitoring a sample, said apparatus comprising:
    an emitter for positioning relative to a sample, wherein said emitter is capable of emitting a light signal directed at the sample;
    a detector for positioning relative to the sample to receive a resulting spectral response signal from the sample following interaction with the light signal;
    a processing element in communication with said detector, wherein said processing element is capable of:
        performing an analysis of the resulting spectral response signal;
        determining a deviation of the spectral response from an expected response;
        comparing the deviation to a threshold; and
        issuing an alert if the value is at least as great as the threshold.

2. An apparatus according to claim 1, wherein said processing element is further capable of determining a cause of the deviation based on performing an analysis of the resulting spectral response signal.

3. An apparatus according to claim 1, wherein said processing element is further capable of determining a value indicating the extent or severity of deviation from the expected response.

4. An apparatus according to claim 1, wherein said processing element is further capable of determining one or more chemical and/or biological agents present in the sample,
    wherein said determining a deviation of the spectral response from an expected response said processor is capable of determining a deviation in the amount of the one or more chemical and/or biological agents from an expected amount.

5. An apparatus according to claim 1, wherein the sample is a flow of gas, and wherein said emitter is capable of emitting a light signal directed at the sample flow.

6. An apparatus according to claim 1, wherein said emitter is a deep UV laser capable of emitting a laser light signal directed at the sample.

7. An apparatus according to claim 1, wherein said detector separates the resulting spectral response signal from the sample into a spectral response output for input to said processing element.

8. An apparatus according to claim 1, wherein the sample is from a gas or air flow, and wherein said apparatus further comprises a sample tube that employs an inlet design and tube design utilizing fluid dynamics to at least one of: filter out wrong-sized particulates, slow down air flow of the sample, or to concentrate the sample prior to testing.

9. An apparatus according to claim 1, wherein said processing element is capable of performing spectrum analysis by analyzing the Raman scattering spectral response of the sample.

10. An apparatus according to claim 1, wherein said processing element is capable of performing spectrum analysis by analyzing the fluorescence spectral response of the sample.

11. An apparatus according to claim 1, wherein said processing element is capable of performing analysis using both Raman scattering analysis and by analyzing the fluorescence in the resulting spectral response signal.

12. An apparatus according to claim 1, wherein said processing element collects measurements from the sample over time and determines a deviation of the spectral response from an expected response.

13. An apparatus according to claim 1, wherein said processing element collects measurements from the sample from different locations within the sample and determines a deviation of the spectral response from an expected response.

14. An apparatus according to claim 1, wherein said processing element collects measurements from the sample over different frequencies and determines from the collected measurements a deviation of the spectral response from an expected response.

15. An apparatus according to claim 1, wherein said processing element collects measurements from the sample over time and detects deviations of the spectral response from an expected response in the sample over time.

16. An apparatus according to claim 1, wherein the sample is from a process, and said processing element issues an alert to a machine controlling the process to alter the process based on the alert.

17. An apparatus according to claim 1, wherein the apparatus is located on a vehicle, and wherein said processing element issues an alert that the vehicle has been exposed.

18. An apparatus according to claim 1, further comprising a transmitter for transmitting the alert issued by said processing element to a remote location.

19. An apparatus according to claim 1, wherein the apparatus is located on a vehicle, and wherein said processing element issues an alert to a system controlling the vehicle for use in taking evasive action.

20. A method for monitoring a sample, said method comprising:
    emitting a light signal directed at a sample using a light source;
    receiving a resulting spectral response signal from the sample following interaction with the light signal using a receiver;
    using a processing element to perform the following:
    performing an analysis of the resulting spectral response signal;
    determining a deviation of the spectral response from an expected response;
    comparing the deviation to a threshold; and
    issuing an alert if the value is at least as great as the threshold.

21. A method according to claim 20 further comprising determining a cause of the deviation based on performing an analysis of the resulting spectral response signal.

22. A method according to claim 20 further comprising determining a value indicating the extent or severity of deviation from the expected response.

23. A method according to claim 20 further comprising determining one or more chemical and/or biological agents present in the sample,
    wherein said determining a deviation of the spectral response from an expected response determines a deviation in the amount of the one or more chemical and/or biological agents from an expected amount.

24. A method according to claim 1, wherein the sample is a flow of gas, and wherein said emitting a light signal emits a light signal directed at the sample flow.

25. A method according to claim 20, wherein said emitting a light signal comprises using a deep UV laser capable of emitting a laser light signal directed at the sample.

26. A method according to claim 20, wherein said receiving a resulting spectral response signal from the sample following interaction with the light signal comprises separating the resulting spectral response signal from the sample into a spectral response output.

27. A method according to claim 20, wherein the sample is from a gas or air flow, and wherein said method comprises filtering the sample to at least one of: filter out wrong-sized particulates, slow down air flow of the sample, or to concentrate the sample prior to testing.

28. A method according to claim 20, wherein said performing an analysis of the resulting spectral response signal comprises performing spectrum analysis by analyzing the Raman scattering spectral response of the sample.

29. A method according to claim 20, wherein said performing an analysis of the resulting spectral response signal comprises performing spectrum analysis by analyzing the fluorescence spectral response of the sample.

30. A method according to claim 20, wherein said performing an analysis of the resulting spectral response signal comprises performing analysis using both Raman scattering analysis and by analyzing the fluorescence in the resulting spectral response signal.

31. A method according to claim 20, wherein said determining a deviation of the spectral response from an expected response comprises collecting measurements from the sample over time and determining from the collected measurements a deviation of the spectral response from an expected response.

32. A method according to claim 20, wherein said determining a deviation of the spectral response from an expected response comprises collecting measurements from the sample from different locations within the sample and determining from the collected measurements a deviation of the spectral response from an expected response.

33. A method according to claim 20, wherein said determining a deviation of the spectral response from an expected response comprises collecting measurements from the sample over different frequencies and determining from the collected measurements a deviation of the spectral response from an expected response.

34. A method according to claim 20, wherein the sample is from a process, and said issuing an output comprises issuing an alert to a machine controlling the process to alter the process based on the alert.

35. A method according to claim 20, wherein the sample is associated with an environment of a vehicle, and wherein said issuing an output comprises issuing an alert that the vehicle has been exposed.

36. A method according to claim 35 further comprising transmitting the alert to a remote location.

37. A method according to claim 20, wherein the sample is associated with an environment of a vehicle, and wherein said issuing an alert comprises issuing an alert to a system controlling the vehicle for use in taking evasive action.

* * * * *